US009662090B2

(12) United States Patent
Eda

(10) Patent No.: US 9,662,090 B2
(45) Date of Patent: May 30, 2017

(54) ULTRASONIC OBSERVATION APPARATUS, OPERATION METHOD OF ULTRASONIC OBSERVATION APPARATUS, AND COMPUTER READABLE RECORDING MEDIUM

(71) Applicant: OLYMPUS CORPORATION, Tokyo (JP)

(72) Inventor: Hirotaka Eda, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/942,163

(22) Filed: Nov. 16, 2015

(65) Prior Publication Data

US 2016/0074008 A1    Mar. 17, 2016

Related U.S. Application Data

(63) Continuation of application No. PCT/JP2014/063395, filed on May 20, 2014.

(30) Foreign Application Priority Data

Jul. 18, 2013    (JP) .................................. 2013-149831

(51) Int. Cl.
*A61B 8/14*    (2006.01)
*A61B 8/00*    (2006.01)
(Continued)

(52) U.S. Cl.
CPC ............ *A61B 8/4444* (2013.01); *A61B 8/145* (2013.01); *A61B 8/4477* (2013.01);
(Continued)

(58) Field of Classification Search
CPC ..... A61B 8/145; A61B 8/4444; A61B 8/5207; G01S 15/895; G01S 7/52033; G01S 7/5205
See application file for complete search history.

(56) References Cited

U.S. PATENT DOCUMENTS 9,028,414 B2    5/2015  Miyaki
2004/0220463 A1    11/2004  Satoh
(Continued)

FOREIGN PATENT DOCUMENTS

EP    2 599 440 A1    6/2013
JP    H02-279145 A    11/1990
(Continued)

OTHER PUBLICATIONS

International Search Report dated Aug. 26, 2014 issued in PCT/JP2014/063395.
(Continued)

*Primary Examiner* — Mark Remaly
(74) *Attorney, Agent, or Firm* — Scully, Scott, Murphy & Presser, P.C.

(57) ABSTRACT

An ultrasonic observation apparatus includes: ultrasound probes; a storage unit that stores, for each ultrasound probe, attenuation that is a difference in signal intensity for each frequency between a predetermined common waveform and a waveform obtained by providing the ultrasound probes with a common transmission drive wave; a transmission drive wave generating unit that generates, for each ultrasound probe, a transmission drive wave obtained by adding the attenuation to the common transmission drive wave; and a reception signal correcting unit that performs a correction for each frequency, by adding the attenuation to a reception signal which is obtained by transmitting to the specimen the transmission echo having the predetermined common waveform and by converting the reception echo reflected from the (Continued)

specimen, the transmission echo being obtained by converting the transmission drive wave that is given by adding the attenuation to the common transmission drive wave.

6 Claims, 14 Drawing Sheets

(51) Int. Cl.
  *G01S 15/89*   (2006.01)
  *G01S 7/52*   (2006.01)
  *A61B 8/08*   (2006.01)
  *B06B 1/02*   (2006.01)

(52) U.S. Cl.
  CPC .............. *A61B 8/5207* (2013.01); *A61B 8/54* (2013.01); *G01S 7/5205* (2013.01); *G01S 7/52033* (2013.01); *G01S 15/895* (2013.01); *A61B 8/4438* (2013.01); *B06B 1/0207* (2013.01)

(56) References Cited

U.S. PATENT DOCUMENTS

| | | |
|---|---|---|
| 2005/0070795 A1 | 3/2005 | Karasawa |
| 2005/0107699 A1 | 5/2005 | Loftman et al. |
| 2012/0310087 A1* | 12/2012 | Miyaki .................. A61B 8/461 600/440 |

FOREIGN PATENT DOCUMENTS

| | | |
|---|---|---|
| JP | H06-015605 U | 3/1994 |
| JP | 2000-279408 A | 10/2000 |
| JP | 2003-325506 A | 11/2003 |
| JP | 2005-270247 A | 10/2005 |
| JP | 3809880 B2 | 8/2006 |
| JP | 2012-250080 A | 12/2012 |
| WO | WO 2012/063929 A1 | 5/2012 |

OTHER PUBLICATIONS

Japanese Office Action dated Mar. 17, 2015 issued in JP 2015-503710.
Japanese Office Action dated Jul. 14, 2015 issued in JP 2015-503710.
English abstract of Japanese Patent Application No. H10-240354.
Extended Supplementary European Search Report dated Feb. 24, 2017 in European Patent Application No. 14 82 6109.2.
Endoh, N. et al., "Experimental Investigation on Improvement of Range Resolution in B-Mode Images by Inverse Filtering Techniques", 1990 Ultrasonics Symposium, Dec. 4, 1990, pp. 1455-1458.
Zhou, S. et al., "Precompensated Excitation Waveforms to Suppress Harmonic Generation in MEMS Electrostatic Transducers", IEEE Transactions on Ultrasonics, Ferroelectrics and Frequency Control, Nov. 1, 2004, vol. 51, No. 11, pp. 1564-1574.
McSweeney, S.G. et al., "Compensation Network Design for Capacitive Ultrasonic Transducers", Jan. 1, 2009, pp. 1-6, retrieved from the Internet: URL:http://ieeexplore.ieee.org/ie15/5510084/5524662/05524696.pdf [retrieved on Feb. 10, 2017].

* cited by examiner

FIG.4
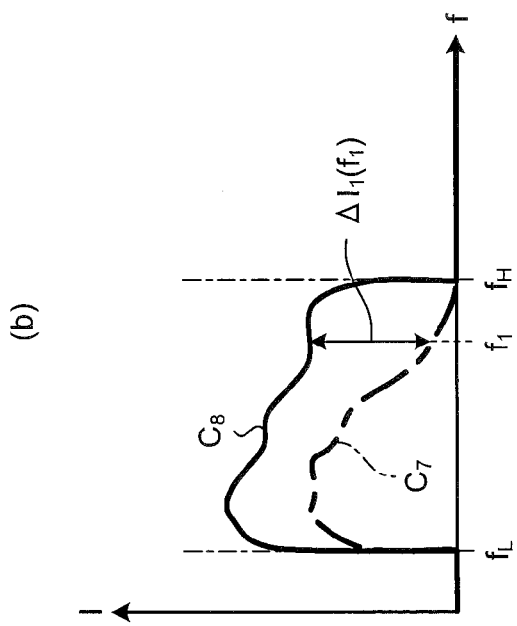
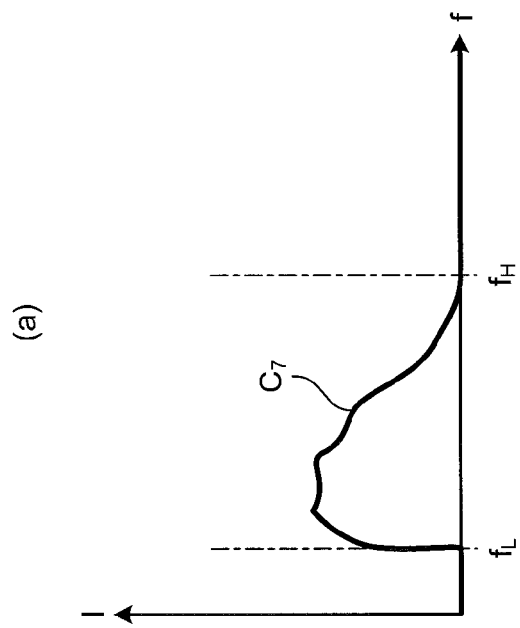

FIG.5
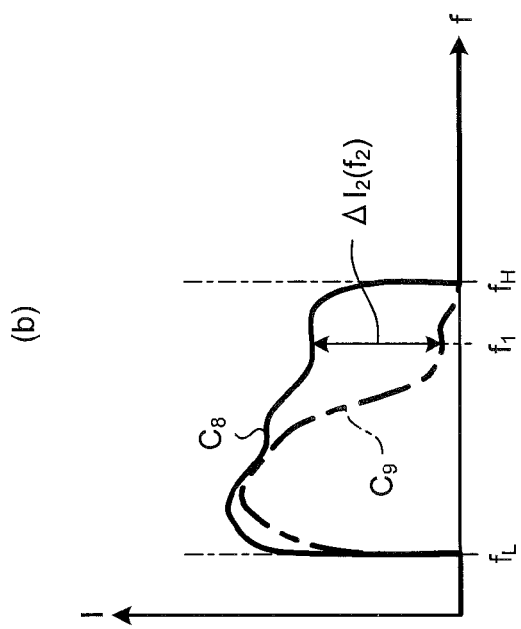
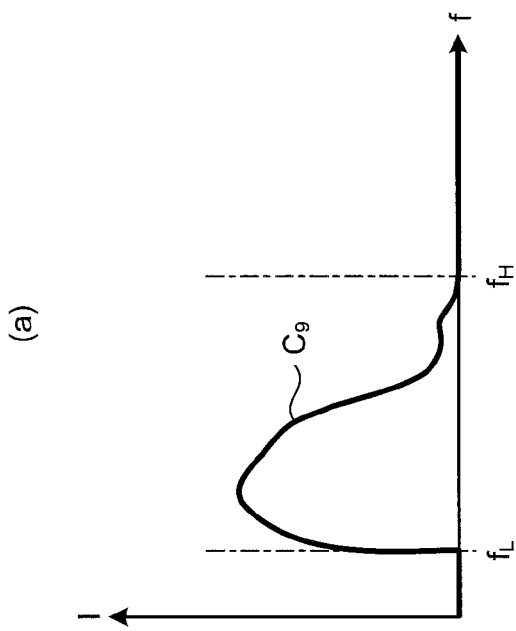

ULTRASONIC OBSERVATION APPARATUS, OPERATION METHOD OF ULTRASONIC OBSERVATION APPARATUS, AND COMPUTER READABLE RECORDING MEDIUM

CROSS REFERENCES TO RELATED APPLICATIONS

This application is a continuation of PCT international application Ser. No. PCT/JP2014/063395 filed on May 20, 2014 which designates the United States, incorporated herein by reference, and which claims the benefit of priority from Japanese Patent Application No. 2013-149831, filed on Jul. 18, 2013, incorporated herein by reference.

BACKGROUND

1. Technical Field

The disclosure relates to an ultrasonic observation apparatus for observing tissues of a specimen using ultrasonic waves, a method for operating the ultrasonic observation apparatus, and a computer readable recording medium.

2. Related Art

In an ultrasonic observation apparatus for generating an ultrasound image of a specimen based on ultrasonic waves, it is preferable that an image displayed in quantitatively evaluating the ultrasound image not be affected by types of an ultrasound probe that transmits and receives ultrasonic waves. In the related art, a technique is known that corrects a reception signal based on frequency characteristics of transducers stored in advance in generating an image using the reception signal in order to suppress variations in transducers of an ultrasonic observation apparatus that generates an ultrasound image of a specimen based on ultrasonic signals (for example, see Japanese Laid-open Patent Publication No. 2012-250080). Another technique is known that monitors a transmission drive signal and corrects the transmission drive signal based on ideal waveform data stored in advance in order to suppress variations in transducers (for example, see Japanese Laid-open Patent Publication No. 2005-270247).

SUMMARY

In some embodiments, an ultrasonic observation apparatus includes: a plurality of ultrasound probes each configured to transmit to a specimen a transmission echo obtained by converting a transmission drive wave which is an electrical signal, to receive a reception echo reflected from the specimen, and to convert the reception echo into a reception signal which is an electrical signal; a storage unit configured to store, for each ultrasound probe, attenuation that is a difference in signal intensity for each frequency between a predetermined common waveform and a waveform obtained by providing the plurality of ultrasound probes with a common transmission drive wave, in order for a waveform of the transmission echo of each of the plurality of ultrasound probes to be the predetermined common waveform; a transmission drive wave generating unit configured to generate, for each ultrasound probe, a transmission drive wave obtained by adding the attenuation to the common transmission drive wave, with reference to the storage unit, in order to transmit to the specimen the transmission echo having the predetermined common waveform; a reception signal correcting unit configured to perform a correction for each frequency with reference to the storage unit, by adding the attenuation to the reception signal which is obtained by transmitting to the specimen the transmission echo having the predetermined common waveform and by converting the reception echo reflected from the specimen, the transmission echo being obtained by converting the transmission drive wave that is given by adding the attenuation to the common transmission drive wave; and an image processing unit configured to form image data using the reception signal corrected by the reception signal correcting unit.

In some embodiments, a method for operating an ultrasonic observation apparatus is provided. The ultrasonic observation apparatus has a plurality of ultrasound probes each configured to transmit to a specimen a transmission echo obtained by converting a transmission drive wave which is an electrical signal, to receive a reception echo reflected from the specimen, and to convert the reception echo into a reception signal which is an electrical signal. The method includes: a transmission drive wave generating step of generating, by a transmission drive wave generating unit, for each ultrasound probe, a transmission drive wave obtained by adding attenuation to a common transmission drive wave, with reference to a storage unit, in order to transmit to the specimen the transmission echo having a predetermined common waveform regardless of types of the ultrasound probes, wherein the storage unit stores, for each ultrasound probe, the attenuation that is a difference in signal intensity for each frequency between the predetermined common waveform and a waveform obtained by providing the plurality of ultrasound probes with the common transmission drive wave; a reception signal correcting step of performing a correction, by a reception signal correcting unit, for each frequency with reference to the storage unit, by adding the attenuation to the reception signal which is obtained by transmitting to the specimen the transmission echo having the predetermined common waveform and by converting the reception echo reflected from the specimen, the transmission echo being obtained by converting the transmission drive wave that is given by adding the attenuation to the common transmission drive wave; and an image processing step of generating, by an image processing unit, image data using the reception signal corrected in the reception signal correcting step.

In some embodiments, a non-transitory computer readable recording medium with an executable program stored thereon is provided. The program instructs an ultrasonic observation apparatus having a plurality of ultrasound probes each configured to transmit to a specimen a transmission echo obtained by converting a transmission drive wave which is an electrical signal, to receive a reception echo reflected from the specimen, and to convert the reception echo into a reception signal which is an electrical signal, to execute: a transmission drive wave generating step of generating, by a transmission drive wave generating unit, for each ultrasound probe, a transmission drive wave obtained by adding attenuation to a common transmission drive wave, with reference to a storage unit, in order to transmit to the specimen the transmission echo having a predetermined common waveform regardless of types of the ultrasound probes, wherein the storage unit stores, for each ultrasound probe, the attenuation that is a difference in signal intensity for each frequency between the predetermined common waveform and a waveform obtained by providing the plurality of ultrasound probes with the common transmission drive wave; a reception signal correcting step of performing a correction, by a reception signal correcting unit, for each frequency with reference to the storage unit, by adding the attenuation to the reception signal which is obtained by transmitting to the specimen the transmission echo having the predetermined common waveform and by converting the reception echo reflected from the specimen, the transmission echo being obtained by converting the transmission drive wave that is given by adding the attenuation to the common transmission drive wave; and an image processing step of generating, by an image processing unit, image data using the reception signal corrected in the reception signal correcting step.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 4 is a diagram illustrating a summary (first example) of a correction process which is performed by a reception signal correcting unit;

FIG. 5 is a diagram illustrating a summary (second example) of the correction process which is performed by the reception signal correcting unit;

DETAILED DESCRIPTION

Hereinafter, modes for carrying out the present invention (hereinafter, referred to as "embodiment(s)") will be described with reference to the accompanying drawings.

First Embodiment

Figure 1:
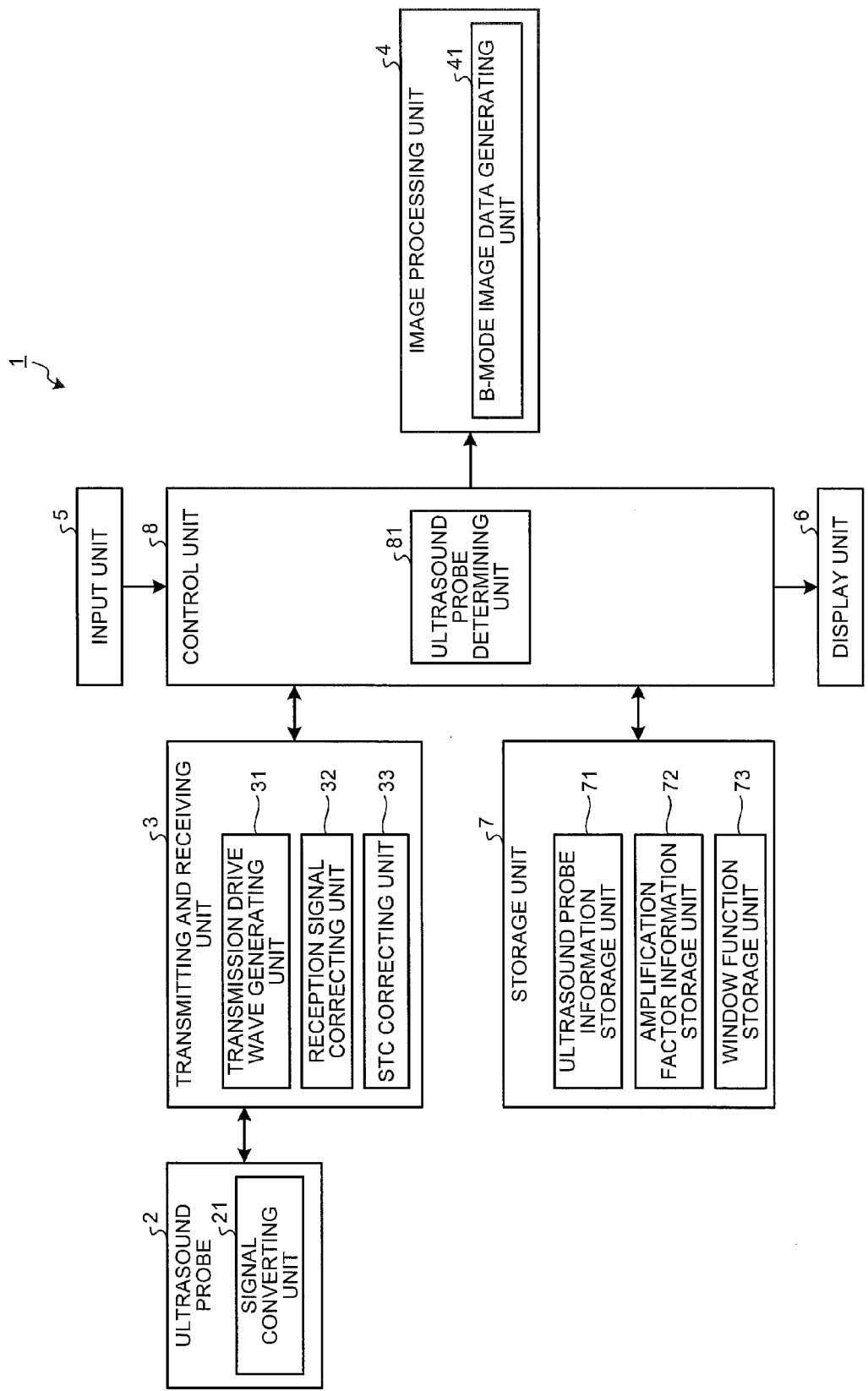
FIG. 1 is a block diagram illustrating a configuration of an ultrasonic observation apparatus according to a first embodiment of the present invention.

FIG. 1 is a block diagram illustrating a configuration of an ultrasonic observation apparatus according to a first embodiment of the present invention. The ultrasonic observation apparatus 1 illustrated in FIG. 1 is an apparatus for observing a specimen as a diagnosis target using ultrasonic waves. The ultrasonic observation apparatus 1 includes an ultrasound probe 2 that outputs a transmission echo of ultrasonic waves to the outside, receives a reception echo of ultrasonic waves reflected from the outside, and converts the received reception echo into an electrical reception signal, a transmitting and receiving unit 3 that transmits and receives an electrical signal to and from the ultrasound probe 2, an image processing unit 4 that generates image data corresponding to the reception signal, an input unit 5 that is embodied by an interface such as a keyboard, a mouse, and a touch panel and receives an input of a variety of information, a display unit 6 that is embodied by a display panel such as a liquid crystal display panel or an organic EL display panel and displays a variety of information including an image generated by the image processing unit 4, a storage unit 7 that stores a variety of information required for ultrasonic observation including parameters indicating characteristics based on the types of the ultrasound probe 2, and a control unit 8 that controls the operation of the ultrasonic observation apparatus 1. The ultrasonic observation apparatus 1 is constituted by a scope in which the ultrasound probe 2 is disposed at a tip thereof and a processing device (processor) to which a base end of the scope is detachably connected and which is provided with the units other than the ultrasound probe 2.

The ultrasound probe 2 includes a signal converting unit 21 that converts a transmission drive wave which is an electrical pulse signal received from the transmitting and receiving unit 3 into a transmission echo which is an acoustic pulse signal and converts a reception echo reflected and returned from an external specimen into an electrical reception signal. In conversion of the transmission drive wave into the transmission echo and conversion of the reception echo into the reception signal, the signal converting unit 21 serves as a filter.

Figure 2:
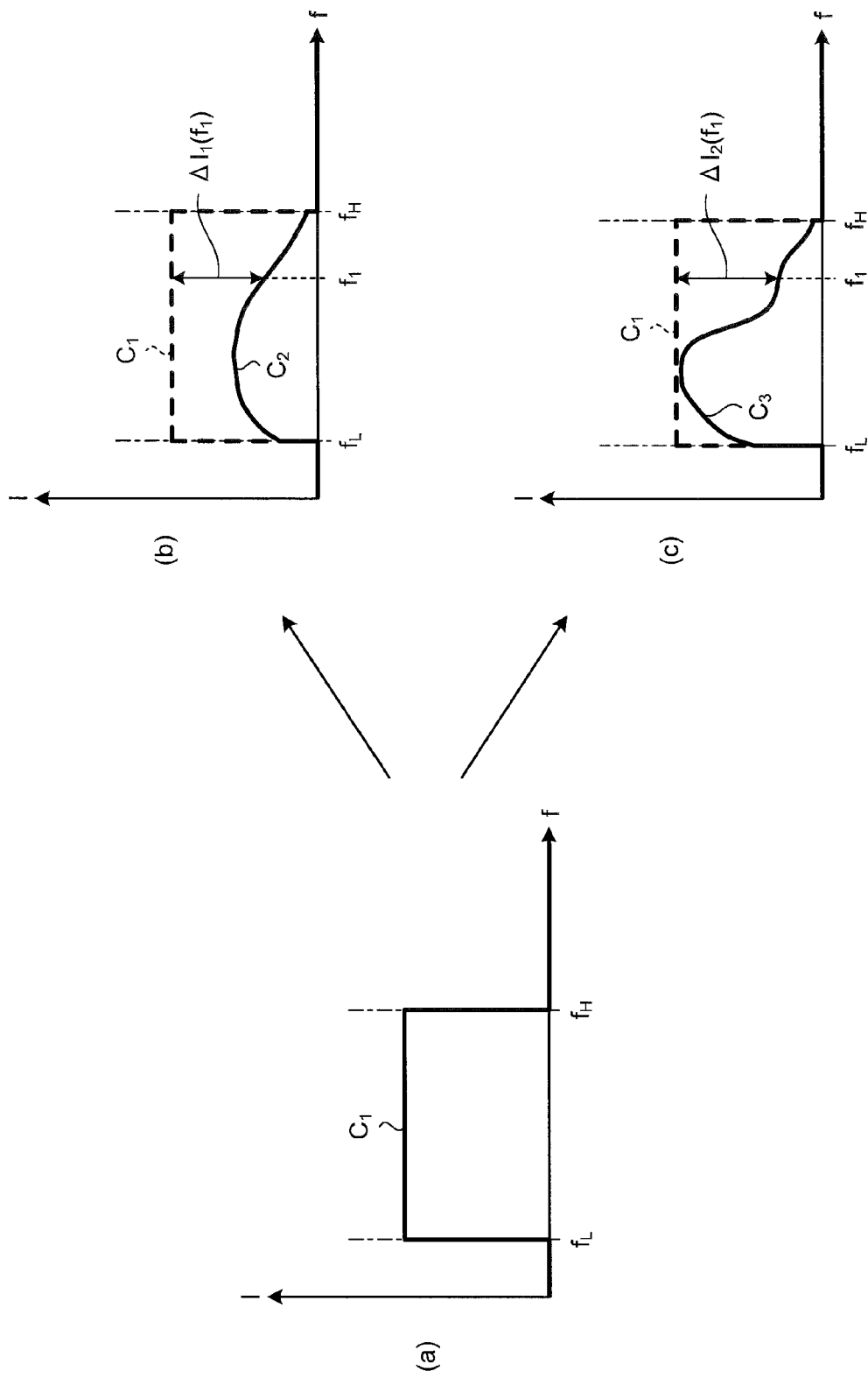
FIG. 2 is a diagram illustrating a variation of a frequency spectrum when a signal converting unit converts a transmission drive wave into a transmission echo.

FIG. 2 is a diagram illustrating a variation of a frequency spectrum when the signal converting unit 21 converts a transmission drive wave into a transmission echo. In FIG. 2($a$), the horizontal axis f denotes frequency and the vertical axis I denotes intensity. A spectrum (frequency spectrum curve) $C_1$ of the transmission drive wave has a rectangular shape having a non-zero constant value in a predetermined frequency band $F=\{f | f_L \leq f \leq f_H\}$. When the transmission drive wave is converted into a transmission echo by the signal converting unit 21, the shape of the spectrum is also changed. FIGS. 2(b) and 2(c) are diagrams illustrating spectra of the transmission echo which are generated by the signal converting units 21 of the ultrasound probes 2 having different types. A spectrum $C_2$ illustrated in FIG. 2(b) has a larger attenuation than a spectrum $C_3$ illustrated in FIG. 2(c).

In the spectrum $C_2$, attenuation $\Delta I_1(f_1)$ corresponding to a difference between the spectrum $C_1$ and the spectrum $C_2$ at a frequency $f_1(f_L \leq f_1 \leq f_H)$ in the frequency band F is stored in an ultrasound probe information storage unit 71 of the storage unit 7 in correlation with the types of the ultrasound probe 2. Similarly, in the spectrum $C_3$, attenuation $\Delta I_2(f_1)$ corresponding to a difference between the spectrum $C_1$ and the spectrum $C_3$ at a frequency $f_1$ in the frequency band F is stored in an ultrasound probe information storage unit 71 in correlation with the types of the ultrasound probe 2. While two ultrasound probes 2 are exemplified herein, attenuation associated with another types of ultrasound probe 2 can also be stored in the ultrasound probe information storage unit 71 in the same way.

Hereinafter, for the purpose of convenience of explanation, it is assumed that the ultrasound probe 2 outputting the spectrum $C_2$ illustrated in FIG. 2(b) as a transmission echo with respect to the transmission drive wave having the spectrum $C_1$ illustrated in FIG. 2(a) is referred to as an ultrasound probe 2A and the ultrasound probe 2 outputting the spectrum $C_3$ illustrated in FIG. 2(c) as a transmission echo is referred to as an ultrasound probe 2B. The signal converting unit 21 of the ultrasound probe 2A is referred to as a signal converting unit 21A and the signal converting unit 21 of the ultrasound probe 2B is referred to as a signal converting unit 21B.

The ultrasound probe 2 may allow an ultrasonic transducer to mechanically scan or may allow plural ultrasonic transducers to electronically scan. In the first embodiment, one ultrasound probe is selectable from different types of ultrasound probes 2 and used as the ultrasound probe 2.

The transmitting and receiving unit 3 is electrically connected to the ultrasound probe 2. The transmitting and receiving unit 3 includes a transmission drive wave generating unit 31 configured to generate a transmission drive wave based on a predetermined waveform and a transmission timing and to transmit the generated transmission drive wave to the ultrasound probe 2, a reception signal correcting unit 32 configured to correct the reception signal received from the ultrasound probe 2 so as to eliminate an influence exerted by a difference in characteristics between the types of the ultrasound probe 2 therefrom, and an STC correcting unit 33 configured to perform STC (Sensitivity Time Control) correction of correcting the reception signal corrected by the reception signal correcting unit 32 with a higher amplification factor as a reception depth is greater.

Figure 3:
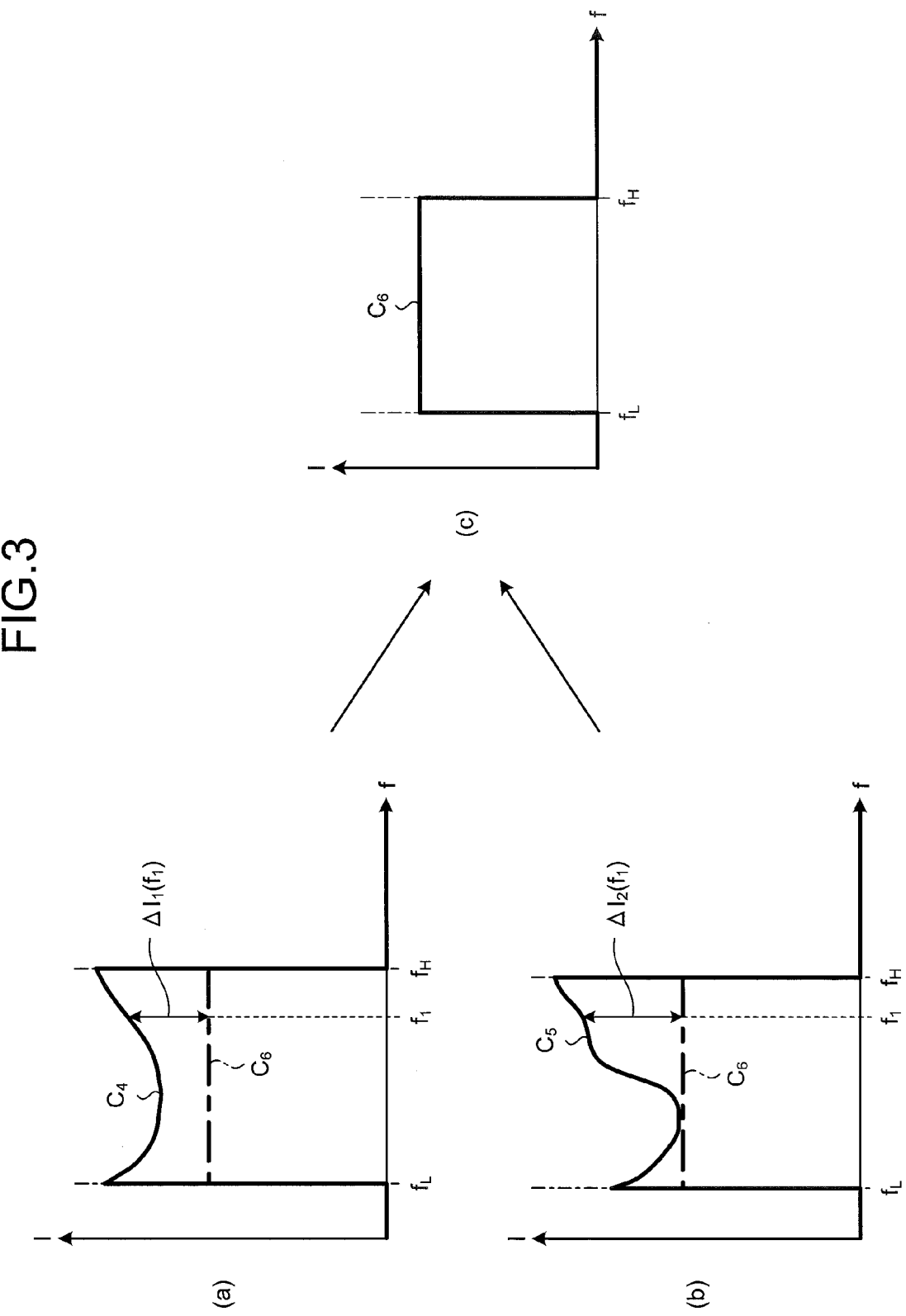
FIG. 3 is a diagram illustrating transmission drive waves generated by a transmission drive wave generating unit and a state in which the signal converting unit of an ultrasound probe converts the transmission drive waves into a transmission echo.

The transmission drive wave generating unit 31 generates a waveform based on characteristics of the ultrasound probe 2 as a transmission drive wave based on information stored in an ultrasound probe information storage unit 71 of the storage unit 7 to be described later. FIG. 3 is a diagram illustrating transmission drive waves generated by a transmission drive wave generating unit 31 and a state in which the signal converting unit 21 of an ultrasound probe 2 converts the transmission drive waves into a transmission echo. The transmission drive wave generating unit 31 may generate different transmission drive waves depending on the types of the ultrasound probe 2. Specifically, the transmission drive wave generating unit 31 reads characteristics depending on the types of the ultrasound probe 2 from the ultrasound probe information storage unit 71 and generates transmission drive waves having spectra $C_4$ and $C_5$ illustrated in FIGS. 3(a) and 3(b), respectively. Here, the characteristics of the ultrasound probe 2 mean information specific to the individual ultrasound probes 2 including attenuation $\Delta I_1(f)$ and $\Delta I_2(f)$ (here, $f \in F$) illustrated in FIGS. 2(b) and 2(c), respectively, and the types of the ultrasound probe 2. In the first embodiment and a second embodiment to be described later, curves and straight lines include sets of discrete points.

The transmission drive wave generating unit 31 generates the transmission drive wave depending on the types of the ultrasound probe 2 based on the spectrum of the generated transmission echo and the characteristics of the ultrasound probe 2. Here, the transmission drive wave generating unit 31 generates transmission drive waves in which a frequency spectrum in a predetermined frequency band of the transmission echo varies depending on the types of the ultrasound probes. The spectrum $C_4$ of the transmission drive wave illustrated in FIG. 3(a) corresponds to the ultrasound probe 2A, and the spectrum $C_5$ of the transmission drive wave illustrated in FIG. 3(b) corresponds to the ultrasound probe 2B. The spectrum $C_4$ has a shape in which attenuation $\Delta I_1(f)$ ($f \in F$) when the ultrasound probe 2A performs conversion is added to the spectrum $C_6$ of the transmission echo. Similarly, the spectrum $C_5$ has a shape in which attenuation $\Delta I_2(f)$ ($f \in F$) when the ultrasound probe 2B performs conversion is added to the spectrum $C_6$ of the transmission echo.

The reception signal correcting unit 32 performs correction depending on the types of the ultrasound probe on the reception signal received from the ultrasound probe 2 by the transmitting and receiving unit 3. FIG. 4 is a diagram illustrating a summary of the correction process which is performed by the reception signal correcting unit 32 and is specifically a diagram illustrating the summary of the correction process which is performed on the reception signal sent from the ultrasound probe 2A. A spectrum $C_7$ illustrated in FIG. 4(a) is a frequency spectrum of a reception signal which is generated by causing the signal converting unit 21A of the ultrasound probe 2A to convert the reception echo. The reception signal correcting unit 32 corrects the reception signal by adding the attenuation $\Delta I_1(f)$ ($f \in F$) when the ultrasound probe 2A performs conversion to the spectrum $C_7$. Accordingly, a spectrum $C_8$ illustrated in FIG. 4(b) is acquired. The spectrum $C_8$ is a spectrum from which the influence by the ultrasound probe 2A is eliminated.

FIG. 5 is a diagram illustrating a summary of the correction process which is performed by the reception signal correcting unit 32 and is specifically a diagram illustrating the summary of the correction process which is performed on the reception signal sent from the ultrasound probe 2B. A spectrum $C_9$ illustrated in FIG. 5(a) is a frequency spectrum of a reception signal which is generated by causing the signal converting unit 21B of the ultrasound probe 2B to convert the reception echo. The reception signal correcting unit 32 corrects the reception signal by adding the attenuation $\Delta I_2(f)$ ($f \in F$) when the ultrasound probe 2B performs conversion to the spectrum $C_9$. Accordingly, a spectrum $C_8$ illustrated in FIG. 5(b) is acquired. The spectrum $C_8$ is a spectrum from which the influence by the ultrasound probe 2B is eliminated and is the same as the spectrum acquired as the result of correction on the reception signal converted by the ultrasound probe 2A (see FIG. 4(b)). In other words, the spectrum $C_8$ is the same as the spectrum of the reception echo.

Figure 6:
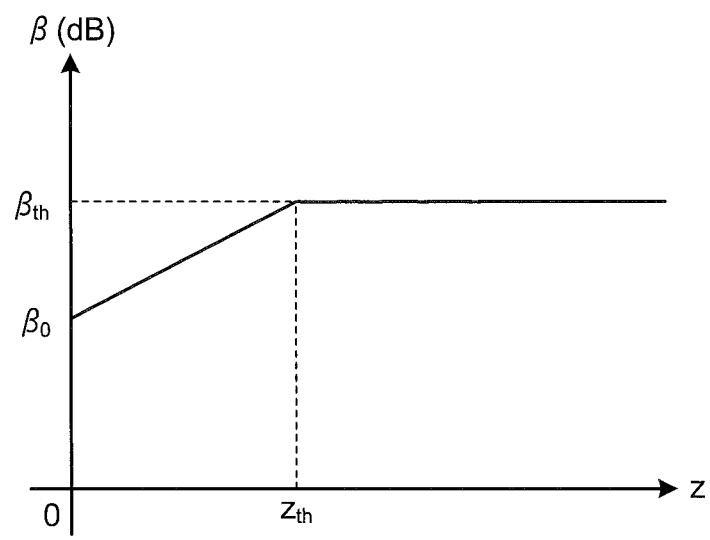
FIG. 6 is a diagram illustrating a relationship between a reception depth and an amplification factor in an amplification process which is performed on a reception signal, which has been corrected by the reception signal correcting unit, by an STC correcting unit.

FIG. 6 is a diagram illustrating a relationship between a reception depth and an amplification factor in an amplification process which is performed on the reception signal, which has been corrected by the reception signal correcting unit 32, by the STC correcting unit 33. The reception depth z illustrated in FIG. 6 is an amount which is calculated based on the elapsed time from the reception start time of ultrasonic waves. As illustrated in FIG. 6, the amplification factor $\beta$ (dB) linearly increases from $\beta_0$ to $\beta_{th}$ ($>\beta_0$) with an increase in the reception depth z when the reception depth z is less than a threshold value $z_{th}$. The amplification factor $\beta$ is retained at a constant value $\beta_{th}$ when the reception depth z is equal to or greater than the threshold value $z_{th}$. The threshold value $z_{th}$ is a value at which the ultrasonic signal received from a specimen is almost attenuated and noise is dominant. More generally, the amplification factor $\beta$ only needs to monotonously increase with an increase in the reception depth z when the reception depth z is less than the threshold value $z_{th}$.

The transmitting and receiving unit 3 generates and outputs a digital RF signal in the time domain by performing a filtering process or the like on the echo signal amplified by the STC correcting unit 33 and then A/D-converting the resultant signal. When the ultrasound probe 2 allows plural ultrasonic transducers to electronically scan, the transmitting and receiving unit 3 includes a beam-synthesis multichannel circuit corresponding to the plural ultrasonic transducers.

The image processing unit 4 includes a B-mode image data generating unit 41 configured to generate B-mode image data from the reception signal.

The B-mode image data generating unit 41 generates B-mode image data by performing signal processing using known techniques such as bandpass filtering, logarithmic conversion, gain processing, and contrast processing on the digital signal and performing data thinning based on a data step width which is determined depending on an image display range in the display unit 6.

The storage unit 7 includes an ultrasound probe information storage unit 71, an amplification factor information storage unit 72, and a window function storage unit 73.

As described above, the ultrasound probe information storage unit 71 stores a correlation between the types of the ultrasound probe 2 and attenuation occurring in the spectrum when the ultrasound probe 2 converts a transmission drive wave into a transmission echo or converts a reception echo into a reception signal as a parameter.

The amplification factor information storage unit 72 stores a relationship (for example, the relationship illustrated in FIG. 2) between an amplification factor and a reception depth, which is referred to by the STC correcting unit 33 at the time of performing an amplification process, as amplification factor information.

The window function storage unit 73 stores at least one window function of window functions such as Hamming, Hanning, and Blackman.

The storage unit 7 is embodied by a ROM in which an operation program of the ultrasonic observation apparatus 1, a program for starting a predetermined OS, or the like is stored in advance, a RAM in which computing parameters or data of processes or the like is stored, and the like.

The control unit 8 includes an ultrasound probe determining unit 81 configured to determine the types of the ultrasound probe 2 connected thereto. The determination result of the ultrasound probe determining unit 81 is stored in the ultrasound probe information storage unit 71 and is referred to when the signal converting unit 21, the transmission drive wave generating unit 31, and the reception signal correcting unit 32 perform processes. In order for the ultrasound probe determining unit 81 to perform the determination, the scope including the ultrasound probe 2 can be provided with a connection pin for causing a processing device in the subsequent stage to determine the types of the ultrasound probe 2 in a connection portion to the processing device. Accordingly, the ultrasound probe determining unit 81 disposed in the processing device can determine the types of the ultrasound probe 2 depending on the shape of the connection pin of the connected scope.

The control unit 8 is embodied by a CPU having computing and control functions. The control unit 8 collectively controls the ultrasonic observation apparatus 1 by reading information stored in the storage unit 7 and various programs including the operation program of the ultrasonic observation apparatus 1 from the storage unit 7 and performing various computing processes associated with the operation method of the ultrasonic observation apparatus 1.

The operation program of the ultrasonic observation apparatus 1 can be recorded on a computer-readable recording medium such as a hard disk, a flash memory, a CD-ROM, a DVD-ROM, and a flexible disk and can be widely distributed. The recording of various programs on the recording medium may be performed when a computer or a recording medium is shipped as a product or may be performed by downloading through a communication network.

Figure 7:
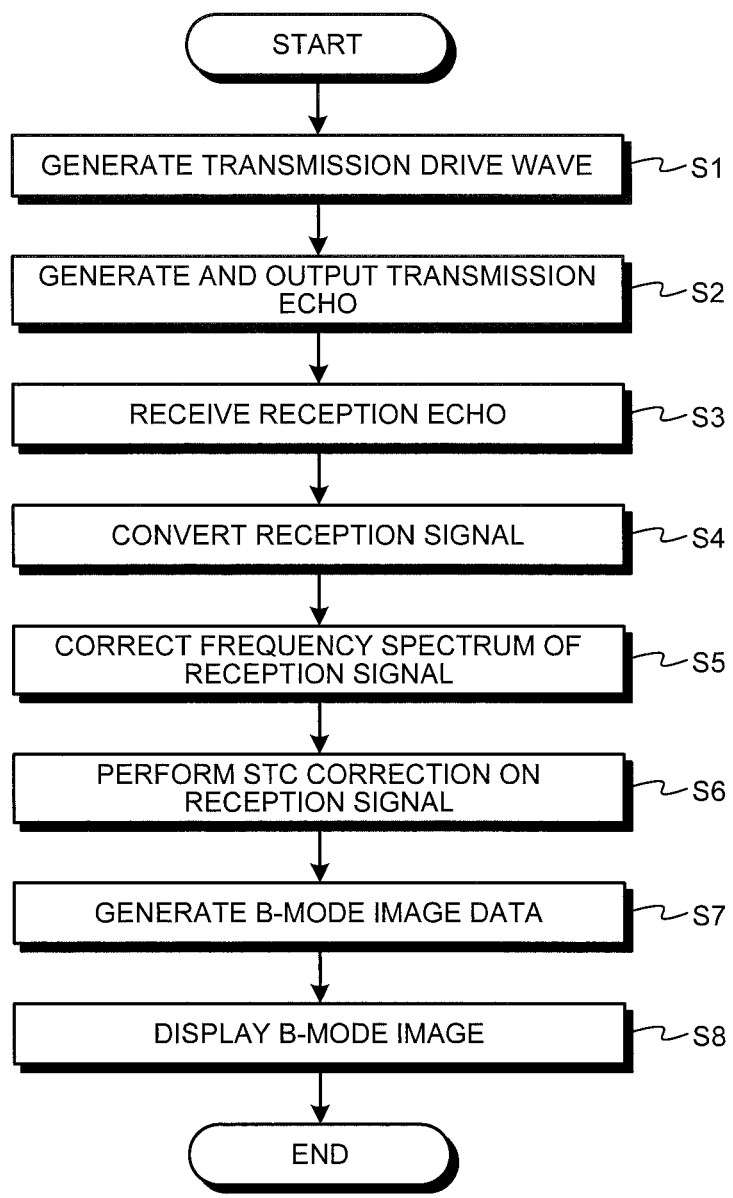
FIG. 7 is a flowchart illustrating a summary of processes in the ultrasonic observation apparatus according to the first embodiment of the present invention.

FIG. 7 is a flowchart illustrating a summary of processes in the ultrasonic observation apparatus 1 having the above-mentioned configuration. It is assumed that the types of the ultrasound probe 2 disposed in the ultrasonic observation apparatus 1 is determined in advance by the ultrasound probe determining unit 81.

In FIG. 7, the transmission drive wave generating unit 31 generates a transmission drive wave and outputs the transmission drive wave to the ultrasound probe 2 (step S1). The spectrum of the transmission drive wave is the spectrum $C_4$ illustrated in FIG. 3(*a*), for example, in case of the ultrasound probe 2A. The spectrum of the transmission drive wave is the spectrum $C_5$ illustrated in FIG. 3(*b*) in case of the ultrasound probe 2B.

Subsequently, in the ultrasound probe 2 receiving the transmission drive wave, the signal converting unit 21 converts the transmission drive wave into a transmission echo and generates and outputs the converted transmission echo (step S2). The spectrum of the transmission echo is, for example, the spectrum $C_6$ illustrated in FIG. 3(*c*). As described above with reference to FIG. 3, the transmission echo has the same spectrum regardless of the types of the ultrasound probe 2.

Thereafter, the ultrasound probe 2 receives a reception echo which is obtained by reflecting and returning the transmission echo from a living body (step S3).

The signal converting unit 21 receiving the reception echo converts the reception echo into a reception signal and outputs the reception signal to the transmitting and receiving unit 3 (step S4). The spectrum of the reception signal is the spectrum $C_7$ illustrated in FIG. 4(*a*), for example, in case of the ultrasound probe 2A. The spectrum of the reception signal is the spectrum $C_9$ illustrated in FIG. 5(*a*) in case of the ultrasound probe 2B.

The reception signal correcting unit 32 receiving the reception signal from the ultrasound probe 2 corrects the frequency spectrum thereof (step S5). The spectrum of the reception signal is the same spectrum regardless of the types of the ultrasound probe 2 (see the spectrum $C_8$ illustrated in FIGS. 4(*b*) and 5(*b*)).

Subsequently, the STC correcting unit 33 performs STC correction on the reception signal of which the spectrum is corrected by the reception signal correcting unit 32 (step S6). Here, the STC correcting unit 33 performs the STC correction, for example, based on the relationship between the amplification factor and the reception depth illustrated in FIG. 6.

Thereafter, the B-mode image data generating unit 41 generates B-mode image data using the echo signal amplified by the STC correcting unit 33 (step S7). The display unit 6 displays a B-mode image corresponding to the B-mode image generated by the B-mode image data generating unit 41 (step S8).

After step S8, the ultrasonic observation apparatus 1 ends a series of processes. The ultrasonic observation apparatus 1 may periodically repeat the processes of steps S1 to S8.

According to the first embodiment of the present invention, since the process of eliminating an influence depending on the types of the ultrasound probe is performed on both the transmission drive wave and the reception signal, it is possible to realize observation of an ultrasound image from which the influence exerted by the difference in types between the ultrasound probes is eliminated.

According to the first embodiment, since the transmission drive wave having a frequency spectrum having a greater value at a frequency at which the attenuation is larger when the transmission drive wave is converted into the transmission echo by the ultrasound probe is generated and the reception signal thereof is corrected based on the attenuation for each frequency, it is possible to satisfactorily eliminate the influence exerted by the difference in characteristics between the types of the ultrasound probes.

Second Embodiment

Figure 8:
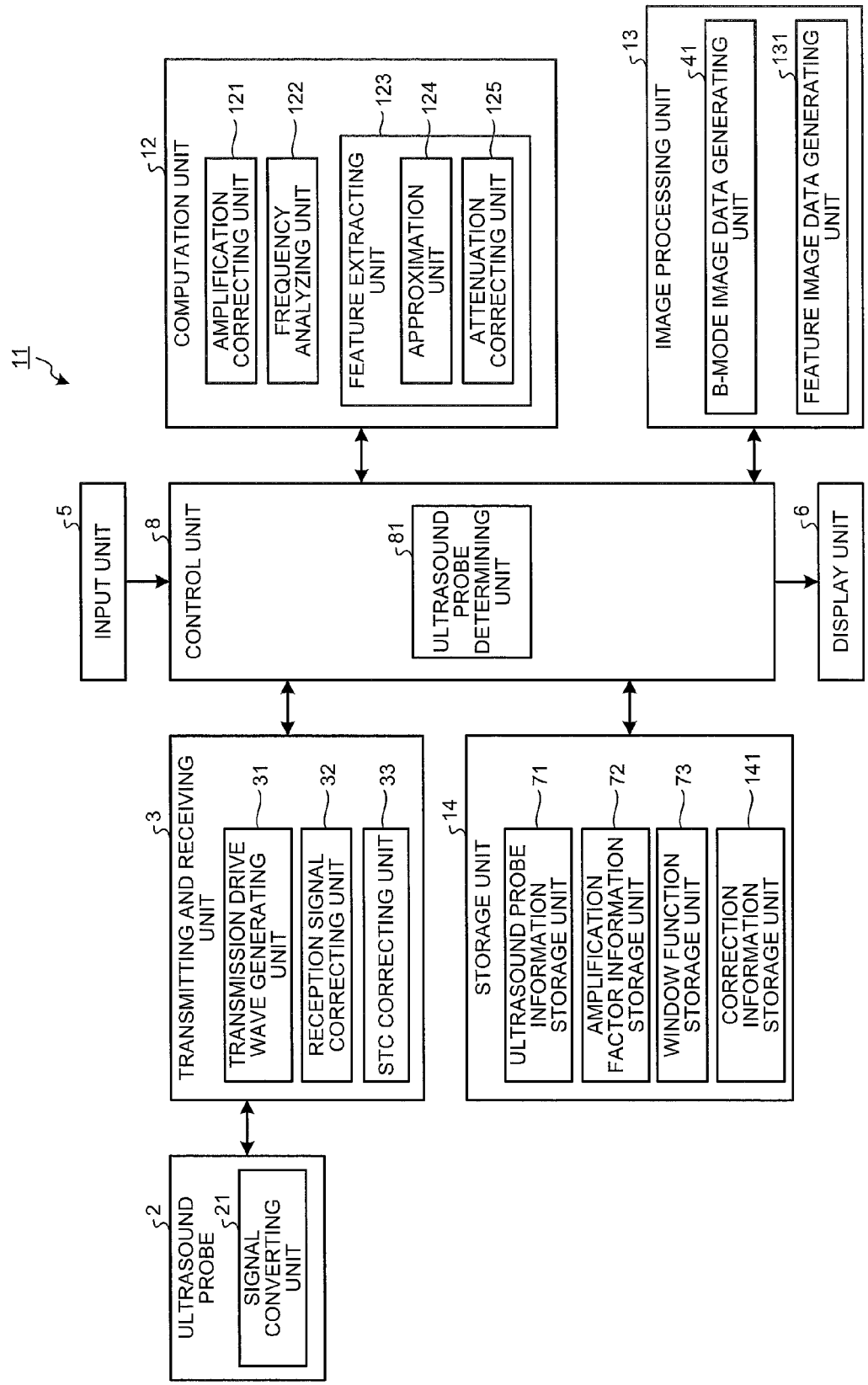
FIG. 8 is a block diagram illustrating a configuration of an ultrasonic observation apparatus according to a second embodiment of the present invention.

FIG. 8 is a block diagram illustrating a configuration of an ultrasonic observation apparatus according to a second embodiment of the present invention. The ultrasonic observation apparatus 11 illustrated in FIG. 8 includes an ultrasound probe 2, a transmitting and receiving unit 3, an input unit 5, a display unit 6, a control unit 8, a computation unit 12 configured to perform a predetermined computation on an electrical reception signal, an image processing unit 13 configured to generate image data corresponding to an electrical echo signal, and a storage unit 14. The same reference signs are used to refer to similar or identical elements to those of the above-described ultrasonic observation apparatus 1.

The computation unit 12 includes an amplification correcting unit 121 configured to perform amplification correction of keeping an amplification factor constant regardless of the reception depth on a digital RF signal output from the transmitting and receiving unit 3, a frequency analyzing unit 122 configured to calculate a frequency spectrum by performing fast Fourier transform (FFT) on the digital RF signal subjected to the amplification correction and performing frequency analysis thereon, and a feature extracting unit 123 configured to extract a feature of a specimen by performing an approximating process based on regression analysis and an attenuation correcting process of reducing a contribution of attenuation occurring depending on the reception depth and the frequency of an ultrasonic wave when the ultrasonic wave propagates on the frequency spectra of respective positions calculated by the frequency analyzing unit 122.

Figure 9:
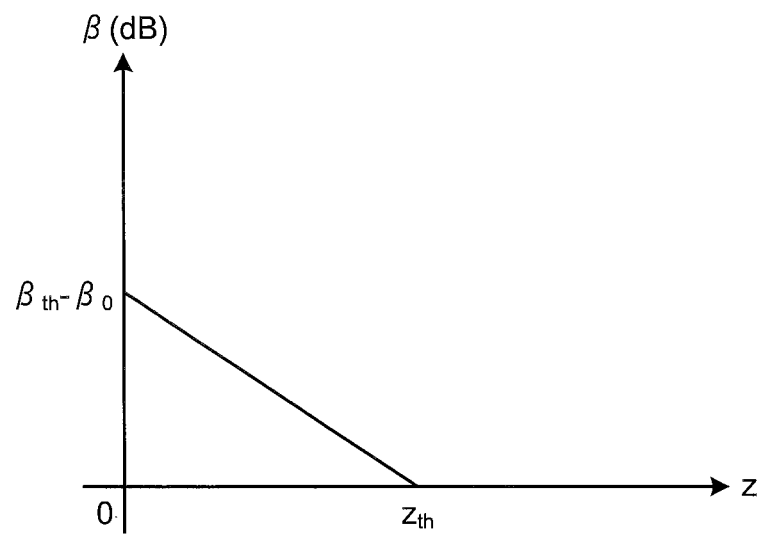
FIG. 9 is a diagram illustrating a relationship between a reception depth and an amplification factor in an amplification process which is performed by an amplification correcting unit.

FIG. 9 is a diagram illustrating a relationship between the reception depth and the amplification factor in the amplification process which is performed by the amplification correcting unit 121. As illustrated in FIG. 9, the amplification factor $\beta$ (dB) in the amplification process which is performed by the amplification correcting unit 121 has a maximum value $\beta_{th}-\beta_0$ when the reception depth z is zero, linearly decreases until the reception depth z moves from zero to the threshold value $z_{th}$, and is zero when the reception depth z is equal to or greater than the threshold value $z_{th}$. Since the amplification correcting unit 121 corrects the amplification of the digital RF signal based on the amplification factor determined in this way, it is possible to cancel the influence of the STC correction in the STC correcting unit 33 and thus to output a signal with a constant amplification factor $\beta_{th}$. The relationship between the reception depth z and the amplification factor $\beta$ in the amplification correcting unit 121 differs depending on the relationship between the reception depth and the amplification factor in the STC correcting unit 33.

The reason for performing this amplification correction will be described below. The STC correction is correction of uniformly amplifying the amplitude of an analog signal waveform in the entire frequency band. Accordingly, a satisfactory B-mode image can be generated using the amplitude of an ultrasonic wave by performing the STC correction, and the influence exerted by attenuation accompanied with the propagation of the ultrasonic wave cannot be satisfactorily eliminated when the frequency spectrum of the ultrasonic wave is calculated. In order to solve this problem, it can be considered that a reception signal subjected to the STC correction is output when the B-mode image is generated and new transmission other than the transmission for generating a B-mode image is performed and a reception signal not subjected to the STC correction is output when an image based on the frequency spectrum is generated. In this case, there is a problem in that the frame rate of the image data generated based on the reception signal is lowered. Accordingly, in the second embodiment, the amplification factor is corrected by the amplification correcting unit 121 to maintain the frame rate of the generated image data and to eliminate the influence of the STC correction from the signal subjected to the STC correction for the B-mode image.

The frequency analyzing unit 122 calculates frequency spectra at plural positions (data positions) on a sound ray by performing fast Fourier transform on FFT data groups having a predetermined amount of data in a sound ray (line data). The calculation result in the frequency analyzing unit 122 is obtained as a complex number and is stored in the storage unit 14.

In general, a frequency spectrum exhibits different tendencies depending on a tissue characterization of a specimen. This is because the frequency spectrum has a correlation with the size, density, acoustic impedance, and the like of a specimen as a scattering body scattering ultrasonic waves. In the second embodiment, the "tissue characterization" is, for example, any one of cancer, endocrine tumor, mucinous tumor, normal tissue, and vascular channel.

Figure 10:
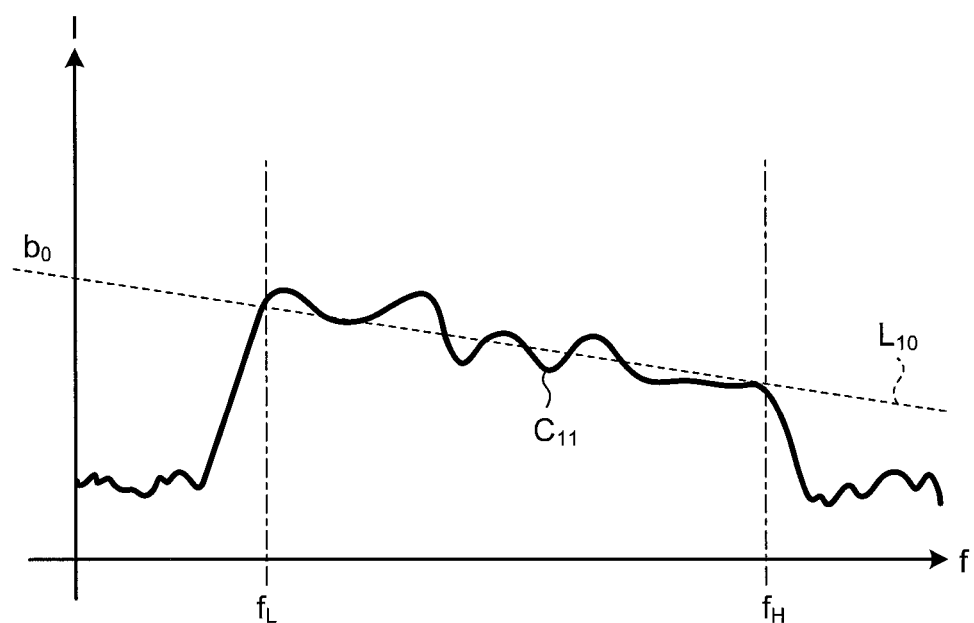
FIG. 10 is a diagram illustrating an example of a frequency spectrum which is calculated by a frequency analyzing unit.

FIG. 10 is a diagram illustrating an example of a frequency spectrum which is calculated by the frequency analyzing unit 122. Specifically, the drawing illustrates a spectrum of an intensity I(f, z) when a frequency spectrum obtained by performing fast Fourier transform on an FFT data group is expressed by an intensity I(f, z) and a phase $\phi$(f, z) as functions of the frequency f and the reception depth z. Here, the "intensity" is any one of parameters such as voltage, power, sound pressure, and acoustic energy. In FIG. 10, the horizontal axis f denotes frequency, the vertical axis I denotes intensity, and the reception depth z is constant. In the spectrum $C_{11}$ illustrated in FIG. 10, a lower-limit frequency $f_L$ and an upper-limit frequency $f_H$ of the frequency spectrum are parameters which are determined based on the frequency band of the ultrasound probe 2 and the frequency band of a pulse signal transmitted from the transmitting and receiving unit 3 and, for example, $f_L$=3 MHz and $f_H$=10 MHz.

The feature extracting unit 123 includes an approximation unit 124 configured to calculate an approximate expression of the frequency spectrum calculated by the frequency analyzing unit 122 using regression analysis and an attenuation correcting unit 125 configured to extract a feature of the frequency spectrum by performing an attenuation correcting process of reducing a contribution of attenuation of an ultrasonic wave depending on the reception depth and the frequency of the ultrasonic wave on the approximate expression calculated by the approximation unit 124.

The approximation unit 124 extracts a feature before the attenuation correction (hereinafter, referred to as a pre-correction feature) characterizing an approximate linear expression by approximating the frequency spectrum calculated by regression analysis using the linear expression (regression line). Specifically, the approximation unit 124 extracts a slope $a_0$ and an intercept $b_0$ of the linear expression as pre-correction features. The straight line $L_{10}$ illustrated in FIG. 10 is a straight line corresponding to the linear expression acquired by the approximation unit 124. The approximation unit 124 may calculate an intensity (also referred to as mid-band fit) $c_0=a_0 f_M+b_0$ at the center frequency $f_M=(f_L+f_H)/2$ of a frequency band ($f_L<f<f_H$) as a pre-correction feature other than the slope $a_0$ and the intercept $b_0$.

It is thought that the slope $a_0$ among three features has a correlation with the size of a scattering body of an ultrasonic wave and generally has a smaller value as the scattering body is larger. The intercept $b_0$ has a correlation with the size of the scattering body, the difference in acoustic impedance, and the density (concentration) of the scattering body. Specifically, it is thought that the intercept $b_0$ has a larger value as the scattering body is larger, has a larger value as the acoustic impedance is larger, and has a larger value as the density (concentration) of the scattering body is larger. The intensity at the central frequency $f_M$ (hereinafter, simply referred to as "intensity") $c_0$ is an indirect parameter which is derived from the slope $a_0$ and the intercept $b_0$ and denotes the spectrum intensity at the center of a valid frequency band. Accordingly, it is thought that the intensity $c_0$ has a certain correlation with the luminance of a B-mode image in addition to the size of the scattering body, the difference in acoustic impedance, and the density of the scattering body. The approximate polynomial calculated by the feature extracting unit 123 is not limited to the linear expression, but a quadratic or higher approximate polynomial may be used.

Figure 11:
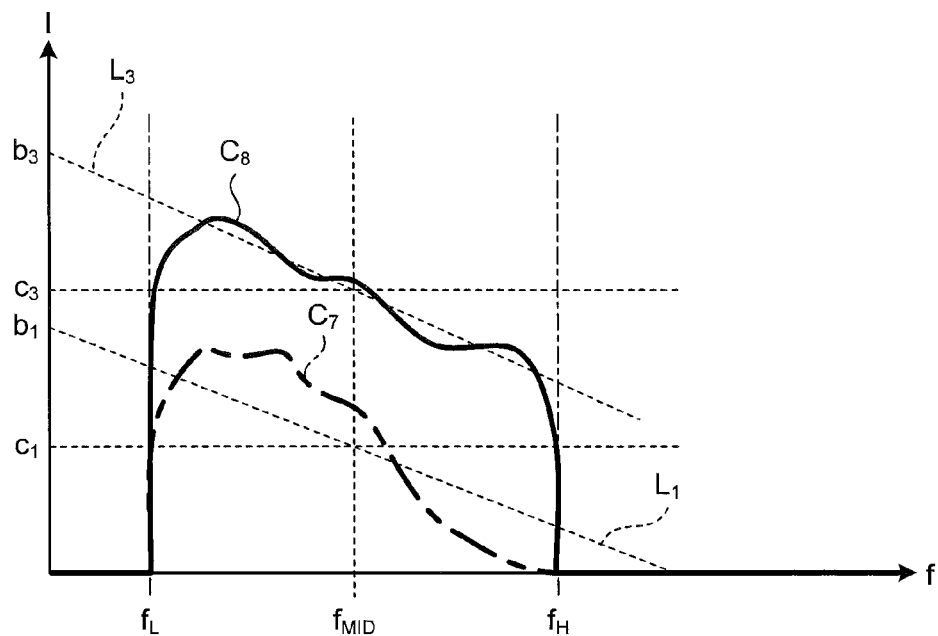
FIG. 11 is a diagram illustrating a frequency spectrum (first example) before and after correction in a reception signal correcting unit when an ultrasound probe is used.
Figure 12:
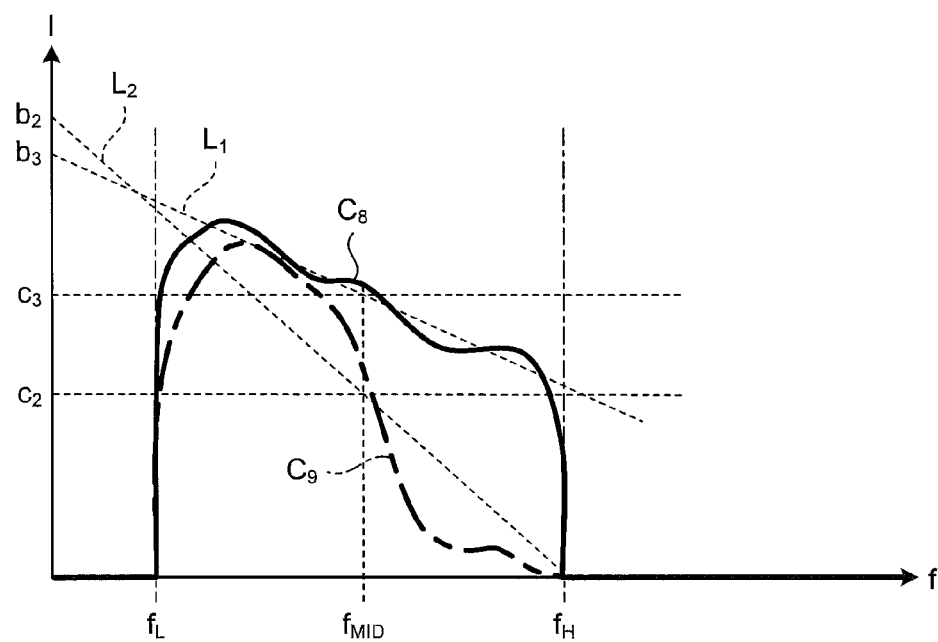
FIG. 12 is a diagram illustrating a frequency spectrum (second example) before and after correction in the reception signal correcting unit when an ultrasound probe is used.
Figure 13:
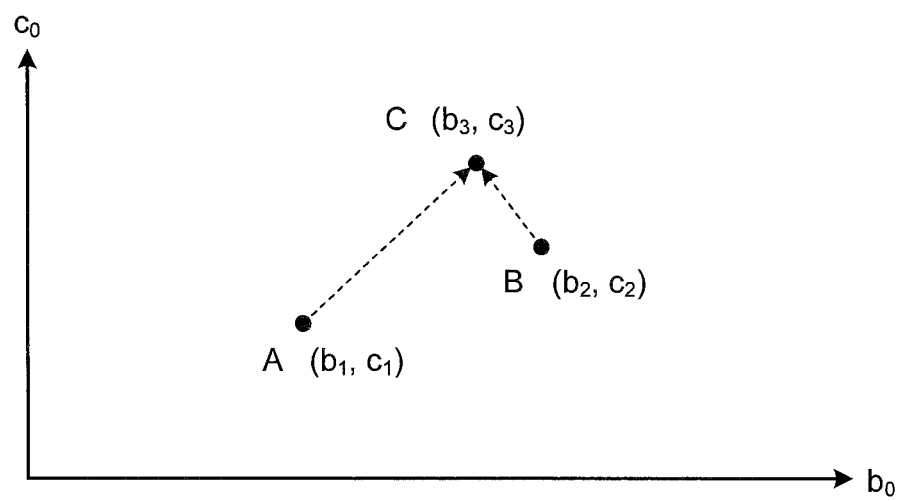
FIG. 13 is a diagram illustrating a state in which features of frequency spectrum curves illustrated in FIGS. 11 and 12 are plotted in a feature space.

It will be described below with reference to FIGS. 11 to 13 that the value of the pre-correction feature is constant regardless of the types of the ultrasound probe 2. In FIGS. 11 to 13, the frequency spectra referred to in the first embodiment are used to describe the cases of two different types of ultrasound probes 2A and 2B. Here, the intercept $b_0$ and the intensity $c_0$ are used as the pre-correction features.

FIG. 11 is a diagram illustrating a frequency spectrum before and after correction in the reception signal correcting unit 32 when the ultrasound probe 2A is used. Specifically, the spectrum $C_7$ is one before the reception signal is corrected and the spectrum $C_8$ is one after the reception signal is corrected. In FIG. 11, the pre-correction features of the spectrum $C_7$ are $b_0=b_1$ (intercept of a straight line $L_1$) and $c_0=c_1$ (intensity of the straight line $L_1$). The pre-correction features of the spectrum $C_8$ are $b_0=b_3$ (intercept of a straight line $L_3$) and $c_0=c_3$ (intensity of the straight line $L_3$).

FIG. 12 is a diagram illustrating a frequency spectrum before and after correction in the reception signal correcting unit 32 when the ultrasound probe 2B is used. Specifically, the spectrum $C_9$ is one before the reception signal is corrected and the spectrum $C_8$ is one after the reception signal is corrected. In FIG. 12, the pre-correction features of the spectrum $C_9$ are $b_0=b_2$ (intercept of a straight line $L_2$) and $c_0=c_2$ (intensity of the straight line $L_2$). In general, $b_2 \neq b_1$ and $b_3$ and $c_2 \neq c_1$ and $c_3$ are established.

FIG. 13 is a diagram illustrating a state in which sets of features of the spectra $C_7$ to $C_9$ illustrated in FIGS. 11 and 12 are plotted in a feature space ($b_0$, $c_0$). As illustrated in FIG. 13, point $A(b_1, c_1)$ which is a set of pre-correction features of the spectrum $C_7$ before the reception signal is corrected and point $B(b_2, c_2)$ which is a set of pre-correction features of the spectrum $C_9$ before the reception signal is corrected are generally different points in the feature space. Since the spectrum corrected by the reception signal correcting unit 32 is the same spectrum $C_8$ regardless of the pre-correction spectrum, a set of post-correction features ($b_0$, $c_0$) is a point $C(b_3, c_3)$ regardless of the pre-correction spectra.

In this way, the pre-correction features of the frequency spectrum of the reception signal are the same because the influence exerted by the frequency spectrum depending on the types of the ultrasound probe 2 is eliminated when the transmission drive wave generating unit 31 generates the transmission drive wave and the influence exerted by the frequency spectrum depending on the types of the ultrasound probe 2 is eliminated from the reception signal by the reception signal correcting unit 32. In this regard, since the influence exerted by the difference in types between the ultrasound probes 2 on the other side not corrected cannot be eliminated by only correcting only one of the transmission drive wave and the reception signal as in the related art, the frequency spectrum of the reception signal varies depending on the types of the ultrasound probe 2. Accordingly, according to the second embodiment, it is possible to satisfactorily eliminate the influence exerted by the difference in type between the ultrasound probes 2 and thus to more accurately extract the features.

The correction which is performed by the attenuation correcting unit 125 will be described below. In general, attenuation A(f, z) of an ultrasonic wave is expressed by the following expression.

$$A(f,z)=2\alpha z f \quad (1)$$

Here, $\alpha$ represents an attenuation factor, z represents the reception depth of an ultrasonic wave, and f represents the frequency. As can be seen from Expression (1), the attenuation A(f, z) is proportional to the frequency f. The specific value of the attenuation factor $\alpha$ ranges 0.0 to 1.0 (dB/cm/MHz) and preferably ranges from 0.3 to 0.7 (dB/cm/MHz) when an observation target is a living body, and is determined depending on portions of the living body. For example, when an observation target is the pancreas, $\alpha$=0.6 (dB/cm/MHz) may be determined. In this embodiment, the value of the attenuation factor $\alpha$ may be set or changed by an input from the input unit 5.

The attenuation correcting unit 125 extracts the features by performing the following attenuation correction on the pre-correction features (the slope $a_0$, the intercept $b_0$, and the intensity $c_0$) extracted by the approximation unit 124.

$$a=a_0+2\alpha z \quad (2)$$

$$b=b_0 \quad (3)$$

$$c=c_0+2\alpha z f_M (=af_M+b) \quad (4)$$

As can be seen from Expressions (2) and (4), the attenuation correcting unit 125 performs correction with a larger degree of correction as the reception depth z of an ultrasonic wave is larger. According to Expression (3), the correction on the intercept is identity transformation. This is because the intercept is a frequency component corresponding to a frequency of 0 (Hz) and is not affected by the attenuation.

Figure 14:
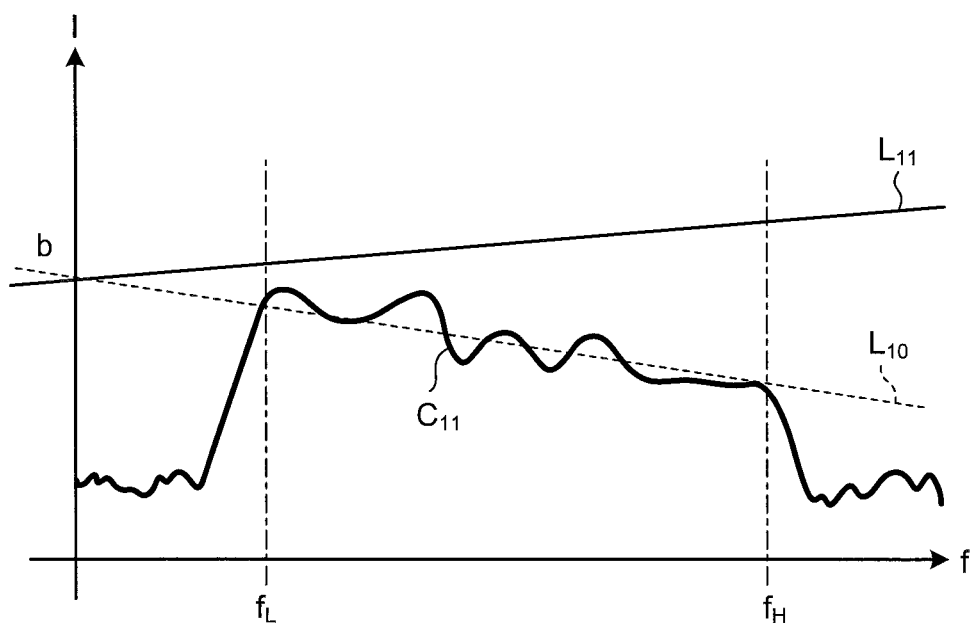
FIG. 14 is a diagram illustrating straight lines corresponding to features which are corrected by an attenuation correcting unit.

FIG. 14 is a diagram illustrating straight lines corresponding to the features which are corrected by the attenuation correcting unit 125. The expression of the straight line $L_{11}$ is as follows.

$$I = af + b = (a_0 + 2\alpha z)f + b_0 \qquad (5)$$

As can be seen from Expression (5), the straight line $L_{11}$ has a larger slope and an equal intercept in comparison with the straight line $L_{10}$.

The image processing unit 13 includes the B-mode image data generating unit 41 and a feature image data generating unit 131 configured to generate feature image data for displaying information corresponding to the features extracted by the feature extracting unit 123 based on any one of plural display methods.

Information which is assigned to pixels in the feature image data in the feature image data generating unit 131 is determined depending on the amount of data of the FFT data group when the frequency analyzing unit 122 calculates the frequency spectrapecifically, information corresponding to the features of the frequency spectrum calculated from an FFT data group is assigned, for example, to a pixel area corresponding to the amount of data of one FFT data group. In the second embodiment, the number of features which are used to generate the feature image data can be arbitrarily set.

The storage unit 14 includes a correction information storage unit 141 in addition to the ultrasound probe information storage unit 71, the amplification factor information storage unit 72, and the window function storage unit 73.

The amplification factor information storage unit 72 stores a relationship (for example, the relationship illustrated in FIG. 6) between the amplification factor and the reception depth which is referred to by the STC correcting unit 33 at the time of performing an amplification process and a relationship (for example, the relationship illustrated in FIG. 9) between the amplification factor and the reception depth which is referred to by the amplification correcting unit 121 at the time of performing the amplification correcting process as amplification factor information.

The correction information storage unit 141 stores information associated with the attenuation correction including Expression (1).

The storage unit 14 is embodied by a ROM in which an operation program of the ultrasonic observation apparatus 11, a program for starting a predetermined OS, or the like is stored in advance, a RAM in which computing parameters or data of processes or the like is stored, and the like.

Figure 15:
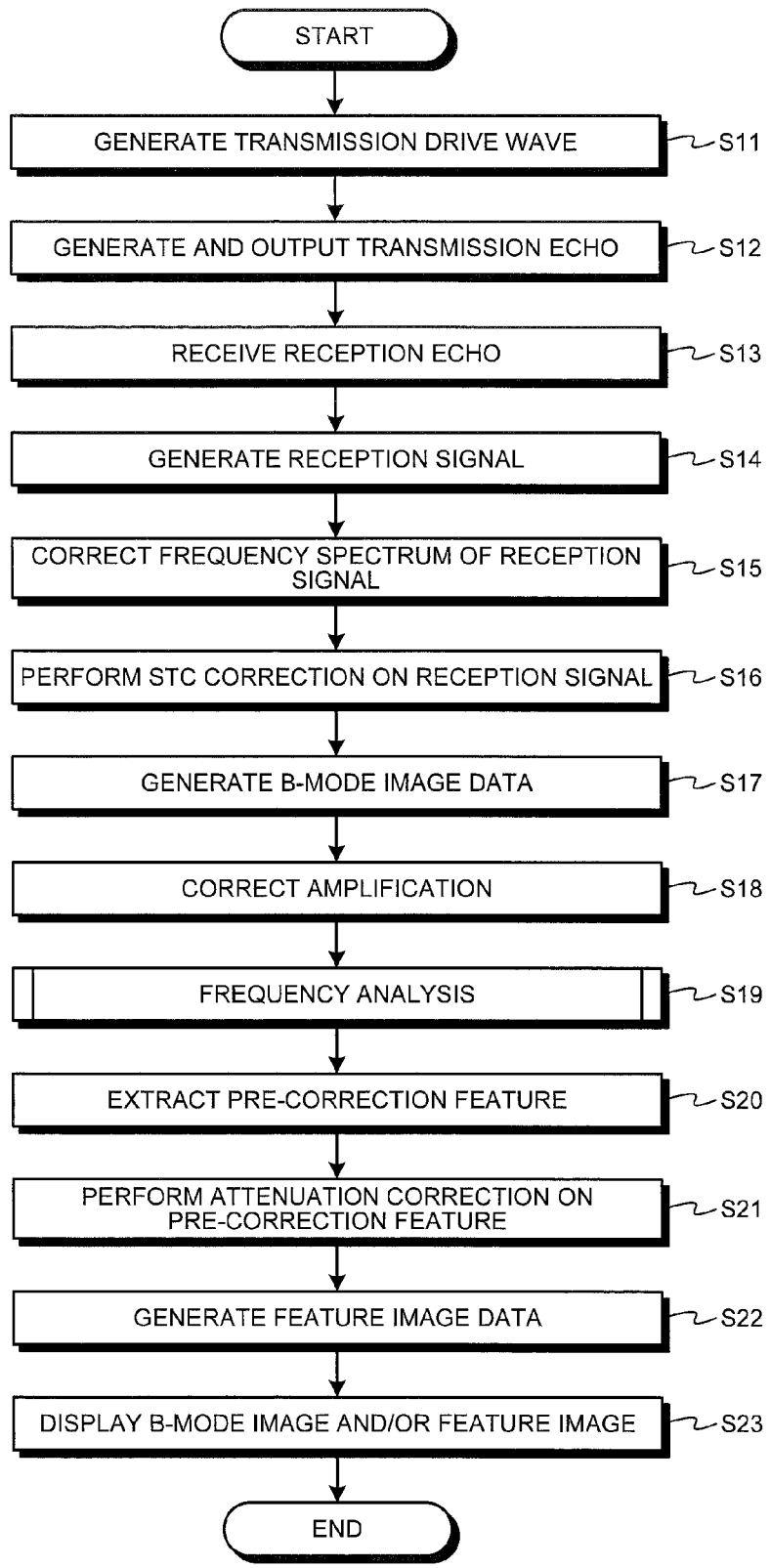
FIG. 15 is a flowchart illustrating a summary of processes in the ultrasonic observation apparatus according to the second embodiment of the present invention.

FIG. 15 is a flowchart illustrating a summary of processes in the ultrasonic observation apparatus 11 having the above-mentioned configuration. In FIG. 15, the processes of steps S11 to S17 respectively correspond to the processes of steps S1 to S7 in the flowchart illustrated in FIG. 7. The processes of step S18 and steps subsequent thereto will be described below.

In step S18, the amplification correcting unit 121 performs the amplification correction in which the amplification factor is constant regardless of the reception depth on the signal output from the transmitting and receiving unit 3 (step S18). Here, the amplification correcting unit 121 performs the amplification correction based on the relationship between the amplification factor and the reception depth illustrated in FIG. 9.

Thereafter, the frequency analyzing unit 122 calculates a frequency spectrum by performing frequency analysis using FFT computation (step S19).

Figure 16:
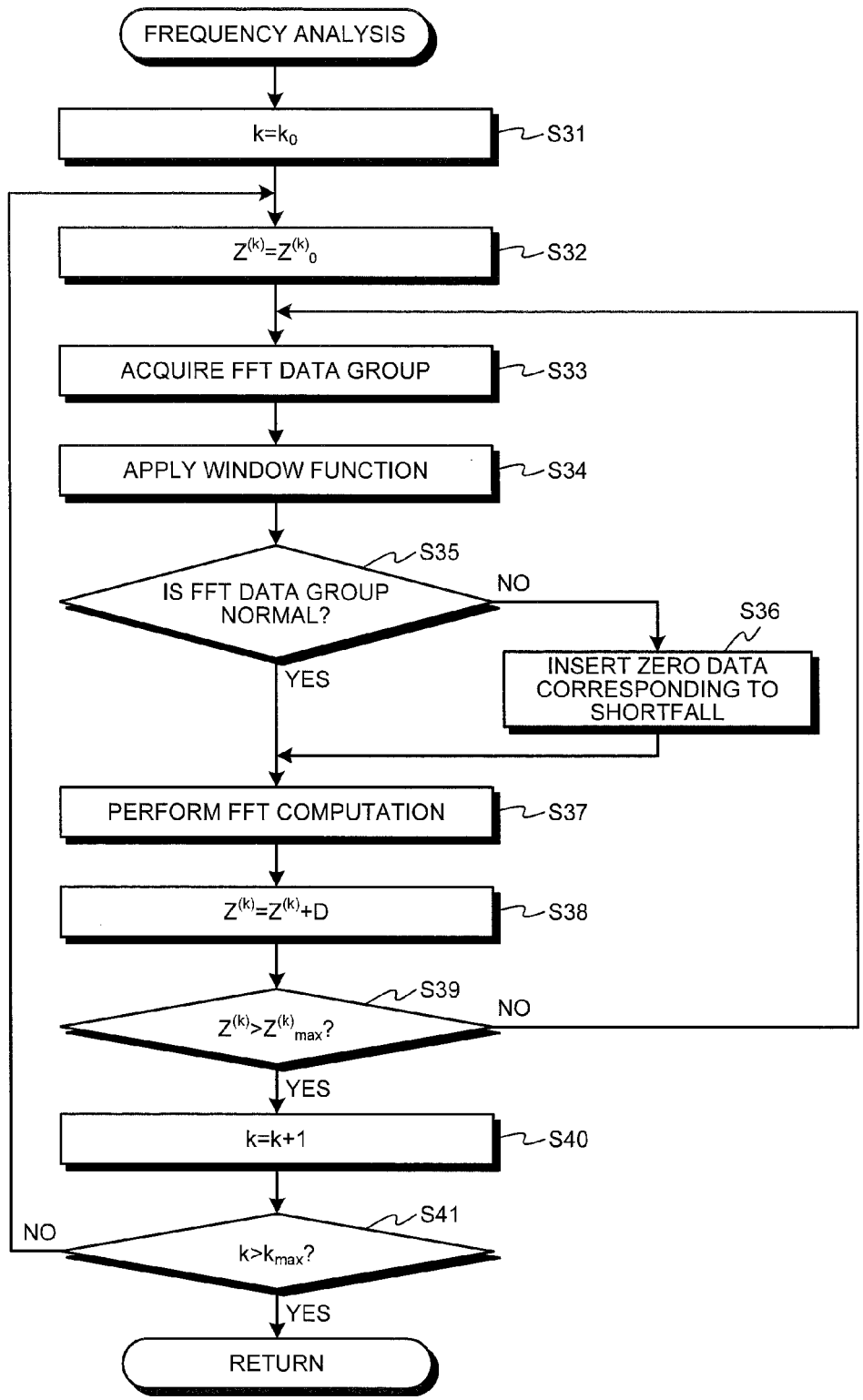
FIG. 16 is a flowchart illustrating a summary of processes which are performed by a frequency analyzing unit.

The process (step S19) which is performed by the frequency analyzing unit 122 will be described below in detail with reference to the flowchart illustrated in FIG. 16. First, the frequency analyzing unit 122 sets a counter k for identifying a sound ray to be analyzed to $k_0$ (step S31).

Figure 17:
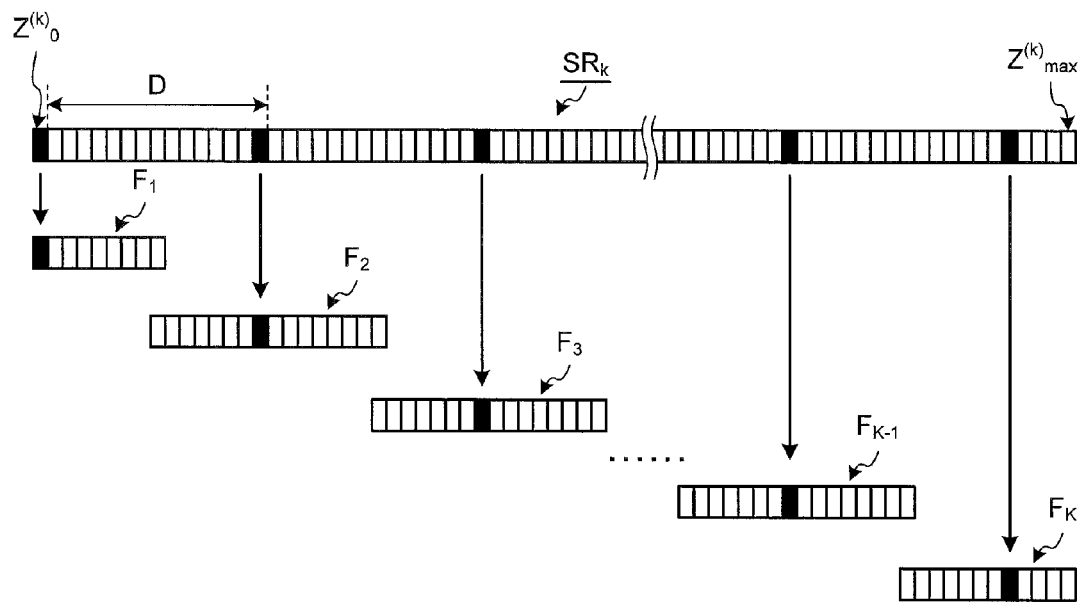
FIG. 17 is a diagram schematically illustrating a data arrangement of a single sound ray.

Subsequently, the frequency analyzing unit 122 sets an initial value $Z^{(k)}_0$ of a data position (corresponding to the reception depth) $Z^{(k)}$ representative of a series of data groups (FFT data groups) acquired for FFT computation (step S32). FIG. 17 is a diagram schematically illustrating a data arrangement of a single sound ray. In the sound ray $SR_k$ illustrated in FIG. 17, white or black rectangles denote one data piece. The sound ray $SR_k$ is discretized at time intervals corresponding to a sampling frequency (for example, 50 MHz) in the A/D conversion which is performed by the transmitting and receiving unit 3. In FIG. 17, the first data position of the sound ray $SR_k$ is set as the initial value $Z^{(k)}_0$, but the position of the initial value can be arbitrarily set.

Thereafter, the frequency analyzing unit 122 acquires the FFT data group of the data position $Z^{(k)}$ (step S33) and applies a window function stored in the window function storage unit 73 to the acquired FFT data group (step S34). By applying the window function to the FFT data group in this way, it is possible to avoid discontinuity at the boundary of the FFT data group and to prevent an artifact from occurring.

Subsequently, the frequency analyzing unit 122 determines whether the FFT data group of the data position $Z^{(k)}$ is a normal data group (step S35). Here, the FFT data group needs to have the number of pieces of data corresponding to a power of two. Hereinafter, the number of pieces of data of the FFT data group is described to be $2^n$ (where n is a positive integer). The FFT data group being normal means that the data position $Z^{(k)}$ is the $2^{n-1}$-th position from the head of the FFT data group. In other words, the FFT data group being normal means that there are $2^{n-1} - 1$ (=N) pieces of data in the front of the data position $Z^{(k)}$ and there are $2^{n-1}$ (=M) pieces of data in the back of the data position $Z^{(k)}$. In FIG. 17, the FFT data groups $F_2$ and $F_3$ are both normal. FIG. 17 exemplifies a case of n=4 (N=7 and M=8).

When it is determined in step S35 that the FFT data group of the data position $Z^{(k)}$ is normal (YES in step S35), the frequency analyzing unit 122 performs the process of step S37 to be described later.

When it is determined in step S35 that the FFT data group of the data position $Z^{(k)}$ is not normal (NO in step S35), the frequency analyzing unit 122 generates a normal FFT data group by inserting pieces of zero data corresponding to the shortfall (step S36). A window function is applied to the FFT data group which is determined to be not normal in step S35 before adding the pieces of zero data thereto. Accordingly, discontinuity of data does not occur even when the pieces of zero data are inserted into the FFT data group. After step S36, the frequency analyzing unit 122 performs the process of step S37 to be described later.

In step S37, the frequency analyzing unit 122 acquires a frequency spectrum including complex number by performing the FFT computation using the FFT data group (step S37). As a result, the spectrum $C_{11}$ illustrated in FIG. 10 is acquired.

Subsequently, the frequency analyzing unit 122 changes the data position $Z^{(k)}$ by a step width D (step S38). It is assumed that the step width D is stored in the storage unit 14 in advance. FIG. 17 exemplifies a case of D=15. The step width D is preferably equal to the data step width used by the B-mode image data generating unit 41 at the time of generating B-mode image data, but may be set to a value greater than the data step width when it is wanted to reduce a computational load in the frequency analyzing unit 122.

Thereafter, the frequency analyzing unit 122 determines whether the data position $Z^{(k)}$ is greater than the maximum value $Z^{(k)}_{max}$ in the sound ray $SR_k$ (step S39). When the data position $Z^{(k)}$ is greater than the maximum value $Z^{(k)}_{max}$ (YES in step S39), the frequency analyzing unit 122 increases the counter k by 1 (step S40). On the other hand, when the data position $Z^{(k)}$ is equal to or less than the maximum value $Z^{(k)}_{max}$ (NO in step S39), the frequency analyzing unit 122 moves back to step S33. In this way, the frequency analyzing unit 122 performs the FFT computation on $[\{(Z^{(k)}_{max}-Z^{(k)}_0)/D\}+1]$ FFT data groups in the sound ray $SR_k$. Here, [X] represents a maximum integer not greater than X.

After step S40, the frequency analyzing unit 122 determines whether the counter k is greater than the maximum value $k_{max}$ (step S41). When the counter k is greater than $k_{max}$ (YES in step S41), the frequency analyzing unit 122 ends a series of FFT processes. On the other hand, when the counter k is equal to or less than $k_{max}$ (NO in step S41), the frequency analyzing unit 122 moves back to step S32.

In this way, the frequency analyzing unit 122 performs the FFT computation on each of $(k_{max}-k_0+1)$ sound rays plural times.

Here, it is on the premise that the frequency analyzing unit 122 performs the frequency analyzing process on the entire region in which the ultrasonic signal is received, but a setting input for a specific region of interest may be received through the input unit 5 in advance and the frequency analyzing process may be performed in the region of interest.

Subsequently to the above-mentioned frequency analyzing process of step S19, the approximation unit 124 extracts pre-correction features by performing regression analysis on the frequency spectra calculated by the frequency analyzing unit 122 as an approximating process (step S20). Specifically, the approximation unit 124 extracts the slope $a_0$, the intercept $b_0$, (and the intensity $c_0$), which characterizes the linear expression, as the pre-correction features by calculating the linear expression approximating the intensity I(f, z) of the frequency spectrum in the frequency band $f_L < f < f_H$ of the frequency spectrum by the regression analysis. The straight line $L_{10}$ illustrated in FIG. 10 is an example of a regression line which is acquired by performing a pre-correction feature extracting process on the spectrum $C_{11}$ in step S20.

Thereafter, the attenuation correcting unit 125 performs the attenuation correcting process on the pre-correction features extracted by the approximation unit 124 (step S21). For example, when the data sampling frequency is 50 MHz, the data sampling time interval is 20 (nsec). Here, when the sound speed is 1530 (m/sec), the data sampling distance interval is 1530 (m/sec)×20 (nsec)/2=0.0153 (mm). When the number of data steps from the first data piece in the sound ray up to the data position of the FFT data group to be processed is n, the data position Z is 0.0153 nD (mm) from the number of data steps n and the data step width D. The attenuation correcting unit 125 calculates the slope a, the intercept b, (and the intensity c) which are features of the frequency spectrum by substituting the value of the data position Z, which are acquired in this way, for the reception depth z of Expressions (2) to (4). The straight line $L_{11}$ illustrated in FIG. 14 is an example of the straight line corresponding to the features calculated in this way.

Steps S20 and S21 described above constitute a feature extracting step of extracting at least one feature from a frequency spectrum by causing the feature extracting unit 123 to approximate the frequency spectrum.

Thereafter, the feature image data generating unit 131 generates feature image data using the features extracted in the feature extracting step (steps S20 and S21) (step S22).

Subsequently, the display unit 6 displays the B-mode image generated by the B-mode image data generating unit 41 and/or the feature image generated by the feature image data generating unit 131 (step S23). At this time, the display unit 6 may display any one of the B-mode image and the feature image, may arrange and display the B-mode image and the feature image, or may overlap and display the B-mode image and the feature image. When the B-mode image and the feature image are overlapped and displayed, a mixing ratio of the B-mode image and the feature image may be changed by an input from the input unit 5.

In this way, by displaying the feature image along with the B-mode image on the display unit 6, a user such as a doctor can determine the tissue characterization of a specimen along with information based on the B-mode image and can perform diagnosis with higher accuracy.

After step S23, the ultrasonic observation apparatus 11 ends a series of processes. The ultrasonic observation apparatus 11 may periodically repeat the processes of steps S11 to S23.

According to the second embodiment of the present invention described above, since the process of eliminating an influence depending on the types of the ultrasound probe is performed on both the transmission drive wave and the reception signal, it is possible to realize observation of an ultrasound image from which the influence exerted by the difference in types between the ultrasound probes is eliminated, similarly to the first embodiment.

According to the second embodiment, since the transmission drive wave having a frequency spectrum having a greater value at a frequency at which the attenuation is larger when the transmission drive wave is converted into the transmission echo by the ultrasound probe is generated and the reception signal thereof is corrected based on the attenuation for each frequency, it is possible to satisfactorily eliminate the influence exerted by the difference in characteristics between the types of the ultrasound probes.

In the second embodiment, the features are extracted by performing the frequency analysis, but a difference in characteristics between the types of the ultrasound probes is excluded from the features. Therefore, according to the second embodiment, there is no influence by the types of the ultrasound probe even in quantitatively evaluating an ultrasound image.

Other Embodiments

Figure 18:
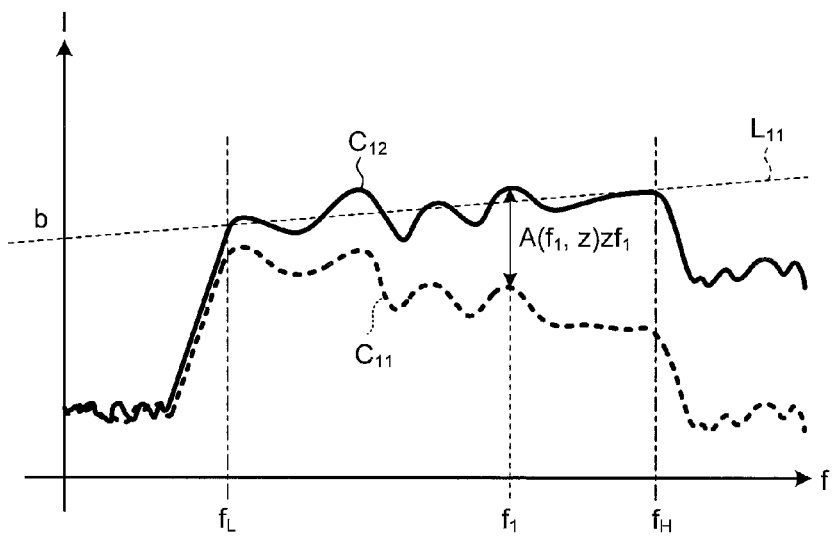
FIG. 18 is a diagram schematically illustrating a summary of an attenuation correcting process which is performed by an attenuation correcting unit of an ultrasonic observation apparatus according to another embodiment of the present invention.

While embodiments of the present invention have been described, the present invention is not limited to the above-mentioned embodiments. For example, in some embodiments, the feature extracting unit 123 may calculate the approximate expression of the corrected frequency spectrum after performing the attenuation correction on the frequency spectrum. FIG. 18 is a diagram schematically illustrating a summary of the attenuation correcting process which is performed by the attenuation correcting unit 125. As illustrated in FIG. 18, the attenuation correcting unit 125 performs a correction process (I(f, z)→I(f, z)+A(f, z)) of adding the attenuation A(f, z) of Expression (1) to the intensity I(f, z) at any frequency f ($f_L < f < f_H$) in the band on the spectrum $C_{11}$. Accordingly, a new spectrum $C_{12}$ is obtained from which a contribution of attenuation due to propagation of ultrasonic waves is reduced. The approximation unit 124 extracts the features by performing the regression analysis on the spectrum $C_{12}$. In this case, the extracted features are the slope a, the intercept b, (and the intensity c) of the straight line $L_{11}$ illustrated in FIG. 18. This straight line is the same as the straight line $L_{11}$ illustrated in FIG. 14.

The control unit 8 may collectively perform the amplification correcting process of the amplification correcting unit 121 and the attenuation correcting process of the attenuation correcting unit 125. These processes are equivalent to the attenuation correcting process of step S21 illustrated in FIG. 15 which is performed by changing the definition of the attenuation to Expression (6) without performing the amplification correcting process of step S18 illustrated in FIG. 15.

$$A' = 2\alpha z f + \gamma(z) \quad (6)$$

Here, γ(z) on the right side represents a difference between the amplification factors β and $β_0$ at the reception depth z and is expressed by the following expressions.

$$\gamma(z) = -\{(\beta_{th} - \beta_0)/z_{th}\}z + \beta_{th} - \beta_0 (z \leq z_{th}) \quad (7)$$

$$\gamma(z) = 0 (z > z_{th}) \quad (8)$$

According to some embodiments, it is possible to realize observation of an ultrasound image from which an influence exerted by a difference in types between ultrasound probes is eliminated.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic observation apparatus comprising:
    a plurality of ultrasound probes each configured to transmit to a specimen a transmission echo obtained by converting a transmission drive wave which is an electrical signal, to receive a reception echo reflected from the specimen, and to convert the reception echo into a reception signal which is an electrical signal; and
    a processor comprising hardware, wherein the processor is configured to:
        reference a storage configured to store, for each ultrasound probe, attenuation that is a difference in signal intensity for each frequency between a predetermined common waveform and a waveform obtained by providing the plurality of ultrasound probes with a common transmission drive wave, in order for a waveform of the transmission echo of each of the plurality of ultrasound probes to be the predetermined common waveform;
        generate, for each ultrasound probe, a transmission drive wave obtained by adding the attenuation to the common transmission drive wave, with reference to the storage, in order to transmit to the specimen the transmission echo having the predetermined common waveform;
        perform a correction process for each frequency with reference to the storage, by adding the attenuation to the reception signal which is obtained by transmitting to the specimen the transmission echo having the predetermined common waveform and by converting the reception echo reflected from the specimen, the transmission echo being obtained by converting the transmission drive wave that is given by adding the attenuation to the common transmission drive wave; and
        form image data using the reception signal corrected by the correction process.

2. The ultrasonic observation apparatus according to claim 1,
    wherein the ultrasound probes are of different types,
    wherein one ultrasound probe is selectable from the different types of ultrasound probes, and
    wherein the storage is configured to store the attenuation depending on the types of ultrasound probes.

3. The ultrasonic observation apparatus according to claim 1,
    wherein the processor is configured to:
        analyze frequencies of an ultrasonic wave received by each of the ultrasound probes to calculate a frequency spectrum;
        approximate the frequency spectrum calculated by the frequency analyzing unit to extract at least one feature from the frequency spectrum; and
        generate feature image data depending on the feature extracted.

4. The ultrasonic observation apparatus according to claim 3,
    wherein the processor is configured to perform an attenuation correcting process of reducing a contribution of attenuation generated depending on a reception depth and a frequency of the ultrasonic wave before or after approximating the frequency spectrum.

5. The ultrasonic observation apparatus according to claim 3,
    wherein the processor is configured to approximate the frequency spectrum using a polynomial by regression analysis.

6. The ultrasonic observation apparatus according to claim 5,
    wherein the processor is configured to approximate the frequency spectrum using a linear expression and to extract, as a feature, at least one of a slope of the linear expression, an intercept of the linear expression, and an intensity which is determined using the slope, the intercept, and a specific frequency included in a frequency band of the frequency spectrum.

* * * * *